(12) United States Patent
Takahashi et al.

(10) Patent No.: US 11,957,300 B2
(45) Date of Patent: Apr. 16, 2024

(54) INFORMATION PROCESSING APPARATUS, CONTROL METHOD, AND PROGRAM

(71) Applicants: NEC CORPORATION, Tokyo (JP); NATIONAL CANCER CENTER, Tokyo (JP)

(72) Inventors: Ikuma Takahashi, Tokyo (JP); Maki Sano, Tokyo (JP); Kimiyasu Takoh, Tokyo (JP); Motoyasu Okutsu, Tokyo (JP); Chiemi Tanaka, Tokyo (JP); Masahiro Saikou, Tokyo (JP); Hitoshi Imaoka, Tokyo (JP); Kenichi Kamijo, Tokyo (JP); Ryuji Hamamoto, Tokyo (JP); Yutaka Saito, Tokyo (JP); Masayoshi Yamada, Tokyo (JP)

(73) Assignees: NEC CORPORATION, Tokyo (JP); NATIONAL CANCER CENTER, Tokyo (JP)

( * ) Notice: Subject to any disclaimer, the term of this patent is extended or adjusted under 35 U.S.C. 154(b) by 517 days.

(21) Appl. No.: 17/274,713

(22) PCT Filed: Sep. 6, 2019

(86) PCT No.: PCT/JP2019/035158
§ 371 (c)(1),
(2) Date: Mar. 9, 2021

(87) PCT Pub. No.: WO2020/054604
PCT Pub. Date: Mar. 19, 2020

(65) Prior Publication Data
US 2022/0051397 A1    Feb. 17, 2022

(30) Foreign Application Priority Data

Sep. 11, 2018   (JP) .................................. 2018-169722

(51) Int. Cl.
*G06T 7/00* (2017.01)
*A61B 1/00* (2006.01)
*H04N 5/272* (2006.01)

(52) U.S. Cl.
CPC ...... *A61B 1/000094* (2022.02); *A61B 1/0005* (2013.01); *G06T 7/0012* (2013.01);
(Continued)

(58) Field of Classification Search
None
See application file for complete search history.

(56) References Cited

U.S. PATENT DOCUMENTS

2011/0123087 A1   5/2011  Nie et al.
2018/0249900 A1*  9/2018  Imaizumi ........... G02B 23/2484
2019/0231444 A1   8/2019  Tojo et al.

FOREIGN PATENT DOCUMENTS

EP   3795062 A1      3/2021
JP   2004-216008 A   8/2004
(Continued)

OTHER PUBLICATIONS

Notice of Reasons for Refusal dated Aug. 2, 2022 from the Japanese Patent Office in JP Application No. 2020-545987.
(Continued)

*Primary Examiner* — Nicholas R Wilson
(74) *Attorney, Agent, or Firm* — Sughrue Mion, PLLC

(57) ABSTRACT

An information processing apparatus (2000) detects an abnormal region (30) from a moving image frame (14). The abnormal region (30) is a region that is estimated to represent an abnormal part inside a body of a subject. The information processing apparatus (2000) generates and outputs output information based on the number of detected abnormal regions (30).

16 Claims, 11 Drawing Sheets

(52) U.S. Cl.
CPC ... *H04N 5/272* (2013.01); *G06T 2207/10068* (2013.01); *G06T 2207/30096* (2013.01)

(56) References Cited

FOREIGN PATENT DOCUMENTS

| | | |
|---|---|---|
| JP | 2011-110429 A | 6/2011 |
| JP | 2011-255006 A | 12/2011 |
| JP | 2015-112429 A | 6/2015 |
| JP | 2016-158681 A | 9/2016 |
| JP | 2017-060806 A | 3/2017 |
| WO | 2018/069992 A1 | 4/2018 |
| WO | 2019/146075 A1 | 8/2019 |

OTHER PUBLICATIONS

Extended European Search Report dated Sep. 9, 2021 from the European Patent Office in EP Application No. 19861116.2.
International Stage Entry of PCT/JP2019/035158 dated Nov. 5, 2019 [PCT/ISA/210].
Written Opinion of PCT/JP2019/035158 dated Nov. 5, 2019 [PCT/ISA/237].

\* cited by examiner

MESHING

DOT PATTERN

MARK INDICATING
CENTER POSITION

RECTANGULAR FRAME

BOUNDARY FRAME

ELLIPTICAL FRAME

INFORMATION PROCESSING APPARATUS, CONTROL METHOD, AND PROGRAM

CROSS REFERENCE TO RELATED APPLICATIONS

This application is a National Stage of International Application No. PCT/JP2019/035158 filed Sep. 6, 2019, claiming priority based on Japanese Patent Application No. 2018-169722 filed Sep. 11, 2018.

TECHNICAL FIELD

The present invention relates to an examination of an inside of a body of a person or other animals using a captured image.

BACKGROUND ART

An examination is performed to find out whether or not there is an abnormality inside a body using an image in which an inside of a body of a person or an animal is imaged. As an example, an endoscope examination is known. In the endoscope examination, a physician inserts a scope provided with a camera at a tip from a nose, a mouse, an anus, or the like of a subject and moves the scope inside a body. In this manner, a state inside the body is imaged by the camera. The physician checks whether or not an abnormal part exists inside the body of the subject while viewing the state inside the body being imaged by the camera using moving image displayed on the display apparatus.

A technique that supports an examination using such an image has been developed. For example, Patent Document 1 discloses a technique that detects a lesion from an image and changes the detected lesion to a color tone different from other parts, thereby enabling easy discrimination of the lesion from other parts. Patent Document 2 discloses a technique that detects a lesion included in an image, computes a degree of seriousness of the lesion, and applies a mark indicating a position or the degree of seriousness of the lesion to the image. Patent Document 3 discloses a technique that, when a lesion is detected from an image, outputs an icon relating to the lesion in a display aspect according to the size of the lesion.

RELATED DOCUMENTS

Patent Documents

[Patent Document 1] Japanese Patent Application Publication No. 2017-060806
[Patent Document 2] Japanese Patent Application Publication No. 2016-158681
[Patent Document 3] Japanese Patent Application Publication No. 2015-112429

SUMMARY OF THE INVENTION

Technical Problem

In the method in which the examination is performed by moving the camera inside the body of the subject, since the camera is moved inside the body, a part that can be observed by the physician changes over time. For this reason, the physician may miss an abnormal part, and there is actually a difference in lesion detection rate depending on physicians in charge of the examination. Accordingly, in order to improve the quality of the examination using an image in which the inside of the body of the subject is imaged, there is demand for various techniques that support the examination.

The present invention has been accomplished in view of the above-described problem. An object of the present invention is to provide a new technique that improves quality of an examination using an image in which an inside of a body of a subject is imaged.

Solution to Problem

An information processing apparatus of the present invention includes 1) a detection unit that detects an abnormal region inside a body from a captured image in which the inside of the body is imaged, and 2) an output unit that generates output information based on the number of the abnormal regions and outputs the generated output information.

A control method of the present invention is executed by a computer. The control method includes 1) a detection step of detecting an abnormal region inside a body from a captured image in which the inside of the body is imaged, and 2) an output step of generating output information based on the number of the abnormal regions and outputting the generated output information.

A program of the present invention causes a computer to execute each step of the control method of the present invention.

Advantageous Effects of Invention

According to the present invention, there is provided a new technique that improves the quality of the examination using an image in which the inside of the body of the subject is imaged.

DESCRIPTION OF EMBODIMENTS

Figure 1:
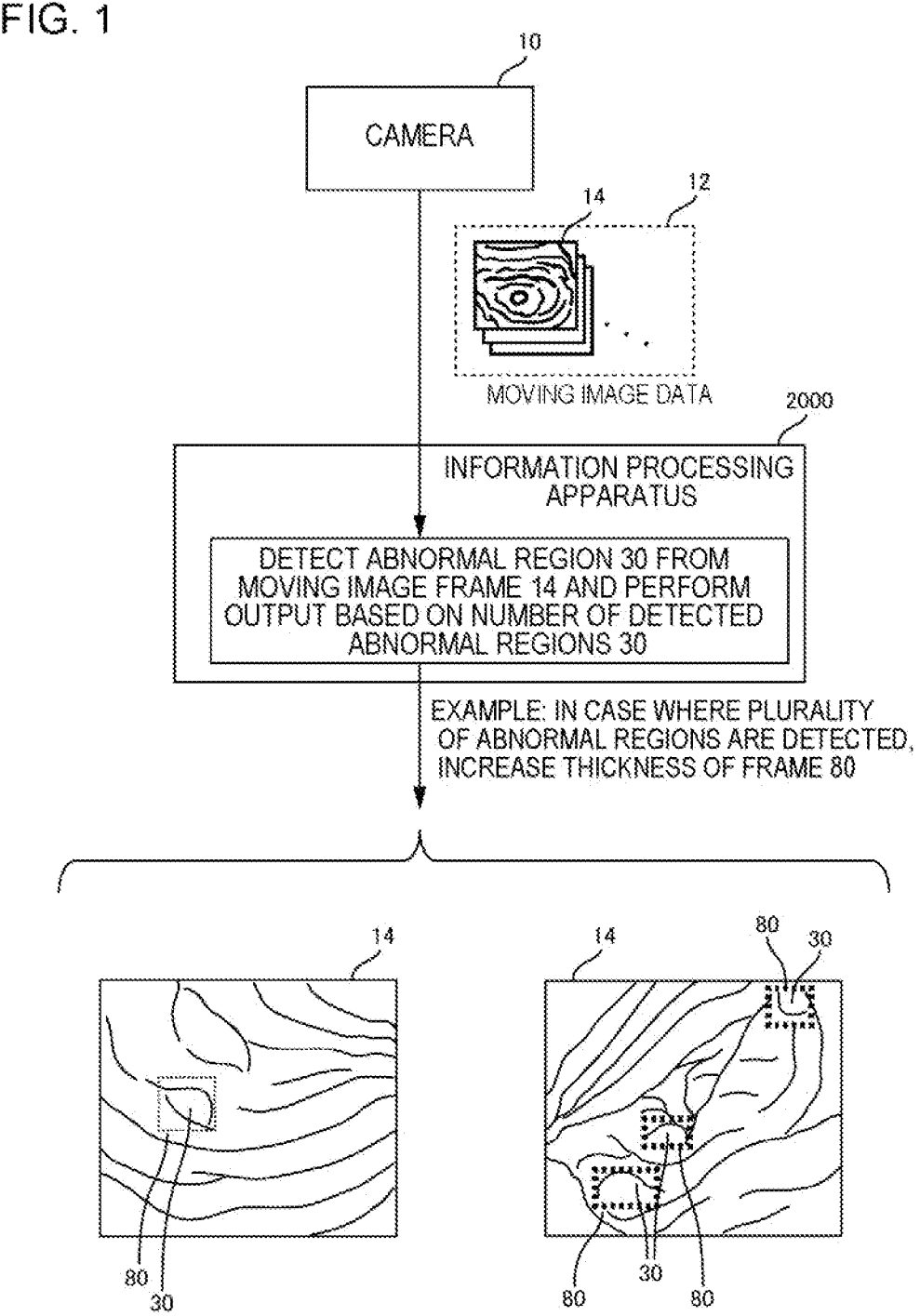
FIG. 1 is a diagram conceptually illustrating an information processing apparatus of Example Embodiment 1.

Hereinafter, an example embodiment of the present invention will be described referring to the drawings. In all drawings, the same components are represented by the same reference numerals, and description thereof will not be repeated. In respective block diagrams, unless particular description is provided, each block is not a configuration of a hardware unit but a configuration of a function unit.

Example Embodiment 1

FIG. 1 is a diagram conceptually illustrating an information processing apparatus 2000 of Example Embodiment 1. It should be noted that FIG. 1 merely shows an example of the operation for ease of understanding of the information processing apparatus 2000, and is not intended to limit the functions of the information processing apparatus 2000.

A camera 10 is used for an examination of a person or other animals. Hereinafter, a person or the like to be examined is referred to as a subject. The camera 10 is any camera that can image an inside of a body of the subject, and generates a moving image frame 14 representing an imaging result. For example, the camera 10 is an endoscope camera. Moving image data 12 is composed of a plurality of moving image frames 14 generated at different times.

A user (for example, a physician) of the information processing apparatus 2000 recognizes a state inside the body of the subject by viewing moving image data 12. More specifically, the user recognizes whether or not there is an abnormal part inside the body of the subject, a degree of abnormality, or the like. Here, "abnormal part inside the body" is, for example, a part having a lesion, a part having a wound, a part having a foreign substance, or the like. The lesion is a change in a living body caused by a disease, and is, for example, a tumor or the like.

Here, useful information obtained by analyzing moving image data 12 is provided, whereby improvement of the accuracy of an endoscope examination or the like can be expected. For example, in the endoscope examination, the physician or the like searches for an abnormal part inside the body while observing the inside of the body of the subject with the camera. In this case, even though an abnormal part is imaged by the camera, the physician may miss the abnormal part. For this reason, it is preferable to perform support such that the physician easily recognizes the abnormal part, and to prevent missing of the abnormal part.

Accordingly, the information processing apparatus 2000 of the example embodiment performs the following operation. First, the information processing apparatus 2000 acquires moving image data 12 and performs image analysis on the moving image frame 14 composing moving image data 12. Specifically, the information processing apparatus 2000 detects an abnormal region 30 from the moving image frame 14. The abnormal region 30 is a region that is presumed to represent an abnormal part inside the body of the subject. For example, the abnormal region 30 of FIG. 1 is a region including a tumor (a region representing a lesion). Then, the information processing apparatus 2000 outputs output information based on the number of detected abnormal regions 30.

The information processing apparatus 2000 performs an output based on the number of abnormal regions 30, thereby making the physician or the like recognize that the number of abnormal regions 30 is not one but is plural or the number of abnormal regions 30 is large. For example, in FIG. 1, the information processing apparatus 2000 processes the moving image frame 14 so as to superimpose a frame 80 on the abnormal region 30, and then, displays the moving image frame 14 on a display apparatus 20. In this case, the thickness of the frame 80 in a case where the number of abnormal regions 30 detected from the moving image frame 14 is plural is made thicker than the thickness of the frame 80 in a case where the number of abnormal regions 30 detected from the moving image frame 14 is one. With this, the physician or the like who views the moving image frame 14 can intuitively recognize that a plurality of abnormal regions 30 are detected.

In this way, with the information processing apparatus 2000, since the output information according to the number of abnormal regions 30 is output, the physician or the like who views the moving image frame 14 can easily recognize information relating to the number of abnormal regions 30. With this, an effect that the physician or the like can be prevented from missing the abnormal region 30 or an effect that the physician or the like can efficiently observe the abnormal region 30 is achieved. Then, an effect that the quality of the examination by the physician or the like is improved is obtained from such an effect.

Hereinafter, the example embodiment will be described in more detail.

<Functional Configuration>

Figure 2:
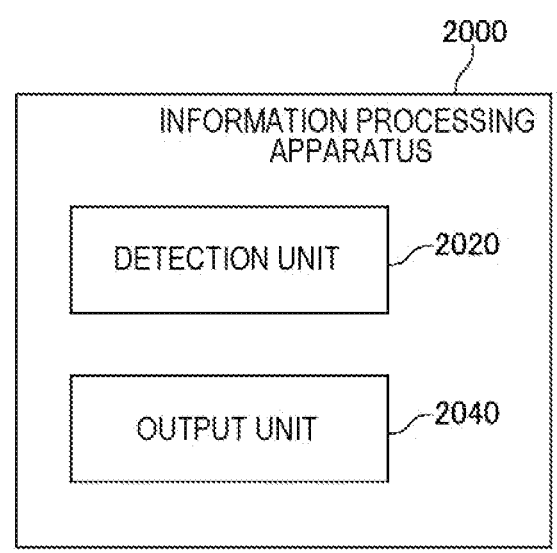
FIG. 2 is a block diagram illustrating the functional configuration of the information processing apparatus.

FIG. 2 is a block diagram illustrating the functional configuration of the information processing apparatus 2000. The information processing apparatus 2000 includes a detection unit 2020 and an output unit 2040. The detection unit 2020 detects the abnormal region 30 from the moving image frame 14. The output unit 2040 outputs the output information based on the number of detected abnormal regions 30.

<Example of Hardware Configuration of Information Processing Apparatus 2000>

Each functional component of the information processing apparatus 2000 may be implemented by hardware (for example, a hard-wired electronic circuit or the like) that implements each functional component or may be implemented by a combination of hardware and software (for example, a combination of an electronic circuit and a program that controls the electronic circuit, or the like). Hereinafter, a case where each functional component of the information processing apparatus 2000 is implemented by a combination of hardware and software will be further described.

Figure 3:
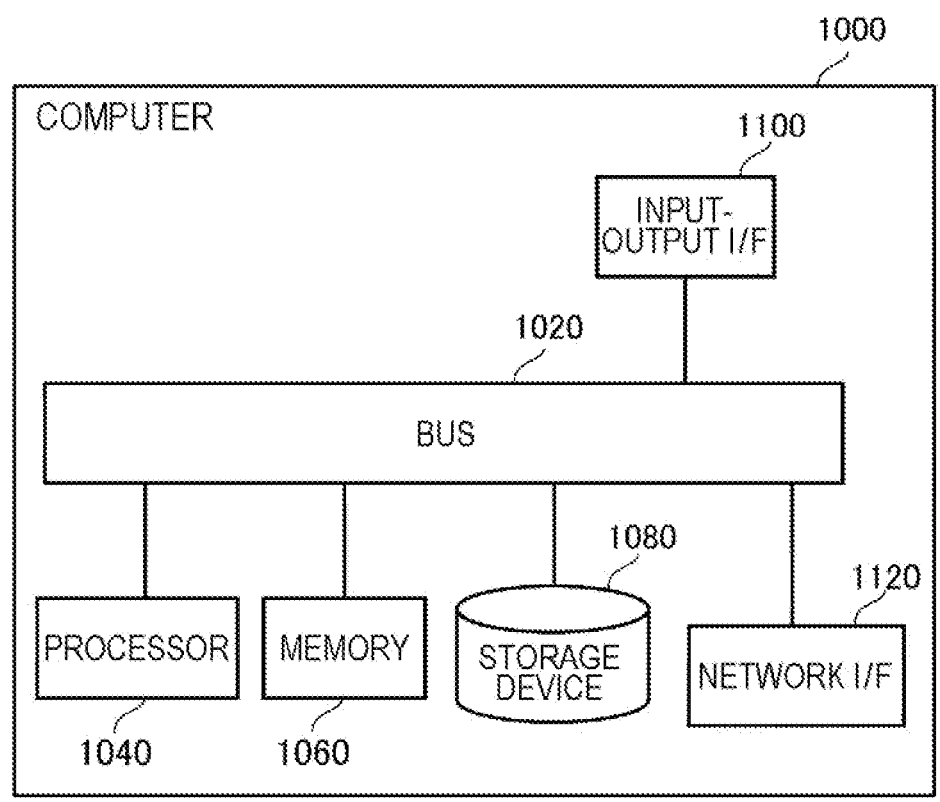
FIG. 3 is a diagram illustrating a computer for implementing the information processing apparatus.

FIG. 3 is a diagram illustrating a computer 1000 for implementing the information processing apparatus 2000. The computer 1000 is any computer. For example, the computer 1000 is a stationary computer, such as a personal computer (PC) or a server machine. In addition, for example, the computer 1000 is a portable computer, such as a smartphone or a tablet terminal. The computer 1000 may be a dedicated computer designed in order to implement the information processing apparatus 2000 or may be a general-purpose computer.

The computer 1000 has a bus 1020, a processor 1040, a memory 1060, a storage device 1080, an input-output interface 1100, and a network interface 1120. The bus 1020 is a data transmission path through which the processor 1040, the memory 1060, the storage device 1080, the input-output interface 1100, and the network interface 1120 transmit and receive data from one another. However, a method of connecting the processor 1040 and the like to one another is not limited to bus connection.

A processor 1040 is various processors, such as a central processing unit (CPU), a graphics processing unit (GPU), and a field-programmable gate array (FPGA). A memory 1060 is a main storage that is implemented using a random access memory (RAM) or the like. A storage device 1080 is an auxiliary storage that is implemented using a hard disk, a solid state drive (SSD), a memory card, or a read only memory (ROM).

The input-output interface 1100 is an interface that connects the computer 1000 and an input-output device. For example, the camera 10 or the display apparatus 20 is connected to the input-output interface 1100.

The network interface 1120 is an interface that connects the computer 1000 to a communication network. The communication network is, for example, a local area network (LAN) or a wide area network (WAN). A method in which the network interface 1120 is connected to the communication network may be wireless connection or may be wired connection.

The storage device 1080 stores a program module that implements each functional component of the information processing apparatus 2000. The processor 1040 reads each program module to the memory 1060 and executes each program module, thereby implementing a function corresponding to each program module.

<Specific Example of Usage Environment of Information Processing Apparatus 2000>

Figure 4:
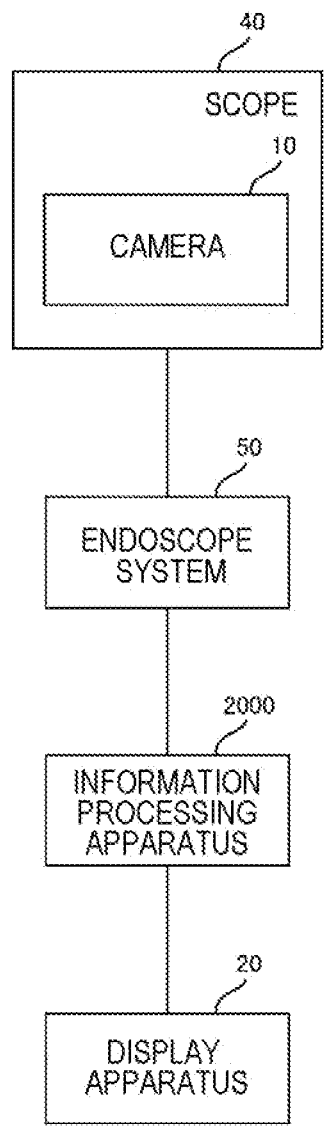
FIG. 4 is a diagram showing a specific example of a usage environment of the information processing apparatus.

FIG. 4 is a diagram illustrating a specific example of a usage environment of the information processing apparatus 2000. For example, the information processing apparatus 2000 is used along with the scope 40 and the endoscope system 50. The scope 40 is connected to the endoscope system 50. The scope 40 is provided with the camera 10. In this case, moving image data 12 is composed of a plurality of moving image frames 14 generated by the camera 10 provided in the scope 40. The endoscope system 50 outputs moving image data 12 to the information processing apparatus 2000. For example, moving image data 12 is output from an interface for video output (for example, a High-Definition Multimedia Interface (HDMI) (Registered Trademark) interface) provided in the endoscope system 50 to an interface for video input in the information processing apparatus 2000. Then, the information processing apparatus 2000 processes moving image data 12 acquired from the endoscope system 50 to generate the output information.

Here, as described below, the output information may be display that is performed using the display apparatus 20 or may be other kinds. In the former case, the information processing apparatus 2000 performs control on the display apparatus 20 such that moving image data 12 is displayed on the display apparatus 20 along with the output information. On the other hand, in the latter case, the processing of displaying moving image data 12 on the display apparatus 20 may be executed by the information processing apparatus 2000 or may be executed by another apparatus (for example, the endoscope system 50). In a case where the processing of displaying moving image data 12 on the display apparatus 20 is executed by the endoscope system 50, the display apparatus 20 does not need to be connected to the information processing apparatus 2000.

The configuration shown in FIG. 4 is merely illustrative, and the usage environment of the information processing apparatus 2000 is not limited to the configuration shown in FIG. 4. For example, the information processing apparatus 2000 may be provided inside the camera 10, the endoscope system 50, or the display apparatus 20. In addition, for example, moving image data 12 may be output from the camera 10 to the information processing apparatus 2000. In this case, the information processing apparatus 2000 may not be connected to the endoscope system 50.

<Flow of Processing>

Figure 5:
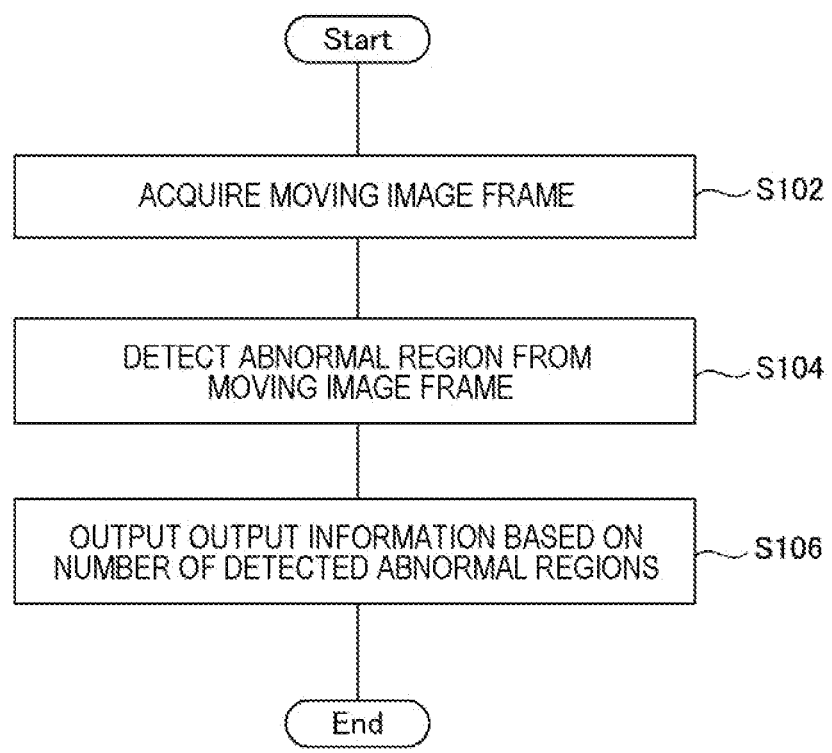
FIG. 5 is a flowchart illustrating a flow of processing that is executed by the information processing apparatus of Example Embodiment 1.

FIG. 5 is a flowchart illustrating a flow of processing that is executed by the information processing apparatus 2000 of Example Embodiment 1. The detection unit 2020 acquires the moving image frame 14 (S102). The detection unit 2020 detects the abnormal region 30 from the acquired moving image frame 14 (S104). The output unit 2040 outputs the output information based on the number of detected abnormal regions 30 (S106).

There are various timings at which a series of processing shown in FIG. 5 is executed. For example, the information processing apparatus 2000 executes the series of processing shown in FIG. 5 each time the moving image frame 14 is generated by the camera 10. In addition, for example, the information processing apparatus 2000 may acquire moving image data 12 from a storage apparatus at a predetermined timing and may execute the series of processing shown in FIG. 5 on each of a plurality of moving image frames 14 composing moving image data 12 (may execute so-called batch processing).

<Acquisition of Moving Image Data 12: S102>

Any method in which the detection unit 2020 acquires moving image data 12 may be used. For example, the detection unit 2020 accesses the storage apparatus in which moving image data 12 is stored, thereby acquiring moving image data 12. The storage apparatus in which moving image data 12 is stored may be provided inside the camera 10 or may be provided outside the camera 10. Alternatively, for example, the detection unit 2020 may receive moving image data 12 transmitted from the camera 10, thereby acquiring moving image data 12. In addition, the detection unit 2020 may acquire moving image data 12 from another apparatus (for example, the above-described endoscope system 50) connected to the camera 10.

<Detection of Abnormal Region 30: S104>

The detection unit 2020 detects the abnormal region 30 from each moving image frame 14 composing moving image data 12. Here, an existing technique can be used as a technique that analyzes the image, in which the inside of the body is imaged, to detect the abnormal part. For example, a method, such as feature value matching or template matching, can be used. For example, in a case of detecting a tumor by feature value matching, one or more values (feature values) representing a feature of an appearance (color, pattern, shape, or the like) of the tumor are defined in advance. The detection unit 2020 detects an image region having high similarity to the feature value of the tumor defined in advance from among image regions of the moving image frame 14. Then, the detection unit 2020 handles the detected image region as an image region representing the abnormal region 30. The same method can be employed in a case of detecting a wound or a foreign substance.

In addition, for example, a detector that detects the abnormal region 30 from the moving image frame 14 may be generated by machine learning, and the abnormal region 30 may be detected using the detector. As a model of the detector, various models, such as a neural network or a support vector machine, can be employed. It should be noted that an existing technique can be used as a technique that generates a detector, which detects a region having a specific feature from an image, by machine learning.

It should be noted that, in a case where a foreign substance is desired to be detected, it is assumed that a foreign substance which entered the inside of the body is identified. In this case, it is preferable that a feature value of the foreign substance can be specified to the information processing apparatus 2000. For example, a photograph of the foreign substance which entered the inside of the body is input to the information processing apparatus 2000. The information processing apparatus 2000 performs image analysis on the photograph, thereby computing the feature value of the foreign substance to be detected. Then, the detection unit 2020 detects the foreign substance having the computed feature value from the moving image frame 14.

<Output of Output Information: S106>

The output unit 2040 counts the number of abnormal regions 30 included in the moving image frame 14 and outputs the output information based on the number of abnormal regions 30 (S106). Hereinafter, the number of abnormal region 30 detected from a certain moving image frame 14 is also denoted as the number of detections for the moving image frame 14.

Here, as the output information based on the number of abnormal regions 30, various kinds of information can be generated. Hereinafter, variation of the output information is illustrated.

<<Output of Number of Abnormal Regions 30>>

Figure 6:
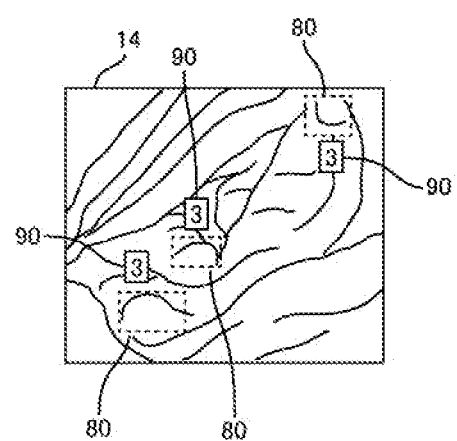
FIG. 6 is a diagram illustrating output information indicating the number of detections.
Figure 7:
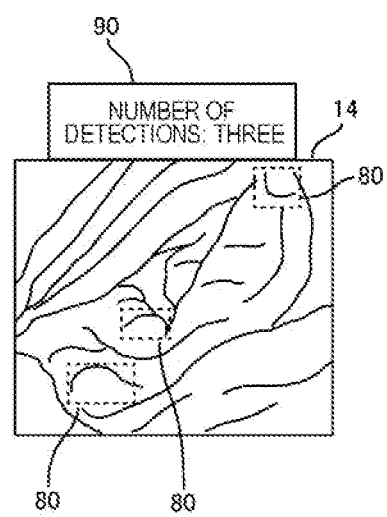
FIG. 7 is a diagram illustrating output information indicating the number of detections.
Figure 8:
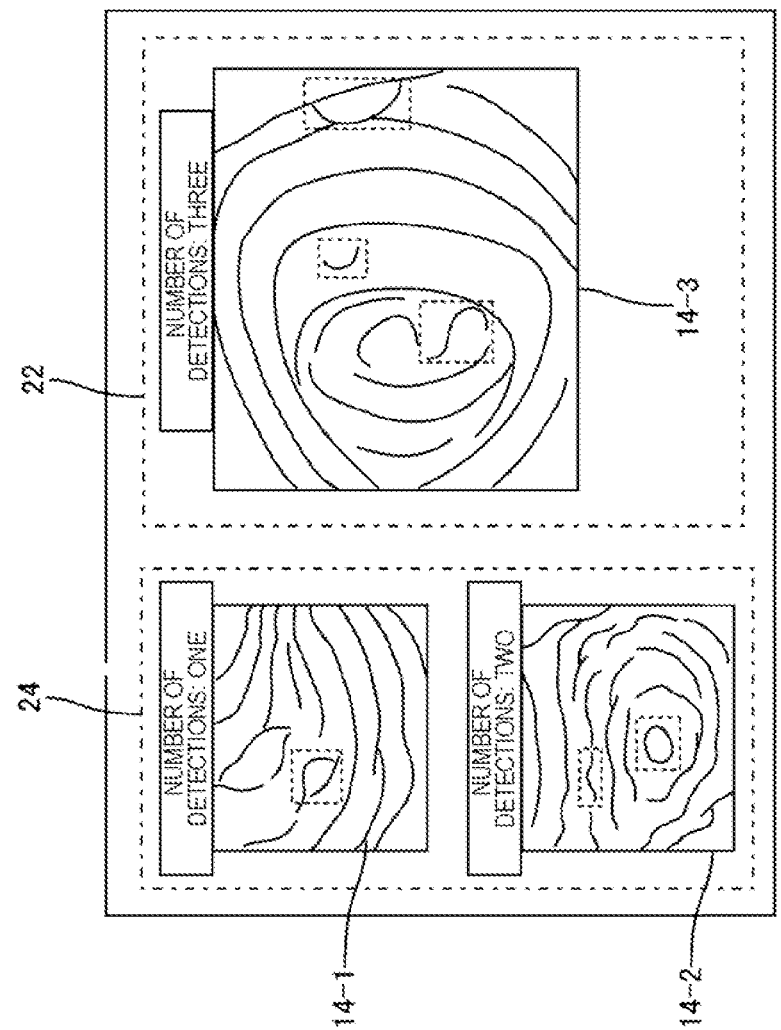
FIG. 8 is diagram illustrating output information indicating the number of detections.

For example, the output unit 2040 generates the output information indicating the number of detections. FIGS. 6 to 8 are diagrams illustrating the output information indicating the number of detections. In FIG. 6, display 90 representing the number of detections is displayed in the vicinity of the frame 80 representing the abnormal region 30.

Here, it is preferable that, for each abnormal region 30 detected from the moving image frame 14, the display 90 representing the number of detections is displayed at a position having a predetermined relationship with the abnormal region 30.

The position having the predetermined relationship with the abnormal region 30 is, for example, the vicinity of the abnormal region 30 (a position at a distance equal to or less than a predetermined value from the abnormal region 30, or the like).

For example, in FIG. 6, three abnormal regions 30 are detected, and display 90-1, display 90-2, and display 90-3 are displayed in the vicinity of the abnormal regions 30, respectively. With this, the physician or the like can easily recognize whether or not the abnormal region 30 other than the abnormal region 30 currently viewed by the physician or the like is detected or the number of abnormal regions 30 (that is, the number of abnormal regions 30 that should be observed by the physician or the like) detected from the moving image frame 14 only by viewing any one abnormal region 30. For example, in FIG. 6, when observing one abnormal region 30, the physician or the like can naturally view the display 90 displayed in the vicinity of the abnormal region 30, and as a result, can recognize that three (two other than the abnormal region 30 under observation) abnormal regions 30 in total are detected.

In FIG. 7, output information is an image in which a moving image frame 14 is included. For example, the image is an image that is displayed on the display apparatus. In FIG. 7, display 90 representing the number of detections is displayed outside the moving image frame 14.

In FIG. 8, output information is an image in which moving image frames 14 are included. In FIG. 8, the moving image frames 14 are displayed in two display regions, respectively. In a display region 22, a latest moving image frame 14 (a moving image frame 14 representing a place being currently imaged by the camera 10) is displayed. On the other hand, in a display region 24, each moving image frame 14 from which abnormal region 30 is detected in the past is displayed. In other words, the display region 24 is a region where a history of the abnormal regions 30 detected so far is displayed.

In FIG. 8, display 90 representing the number of detections is displayed for each moving image frame 14 of the display region 22 and the display region 24. Here, as a method itself of displaying the number of detections for each moving image frame 14, a method of displaying the number of detections in the vicinity of the frame 80 illustrated in FIG. 6, a method of displaying the number of detections outside the moving image frame 14 illustrated in FIG. 7, or the like can be employed. In FIG. 8, outside each moving image frame 14, the number of abnormal regions 30 detected from the moving image frame 14 is displayed.

It should be noted that the moving image frames 14 displayed in the display region 24 may be some of the moving image frames 14 from which the abnormal regions 30 are detected, not all the moving image frames 14. For example, for a plurality of moving image frames 14 in which the same abnormal regions 30 are included, any one moving image frame may be displayed in the display region 24.

For example, the output unit 2040 outputs the image including the display 90 and the moving image frame 14 to the display apparatus connected to the information processing apparatus 2000. In addition, for example, the output unit 2040 may store the image including the display 90 and the moving image frame 14 in the storage apparatus.

<<Highlighting>>

The output unit 2040 may perform highlighting in a case where the number of detections is equal to or greater than a threshold value. Here, in a case where the threshold value is 2, the processing corresponds to processing of "performing highlighting in a case where a plurality of abnormal regions 30 are detected from one moving image frame 14". It should be noted that the threshold value may be set in advance in the output unit 2040 or may be stored in a storage apparatus that is accessible from the output unit 2040.

Figure 9:
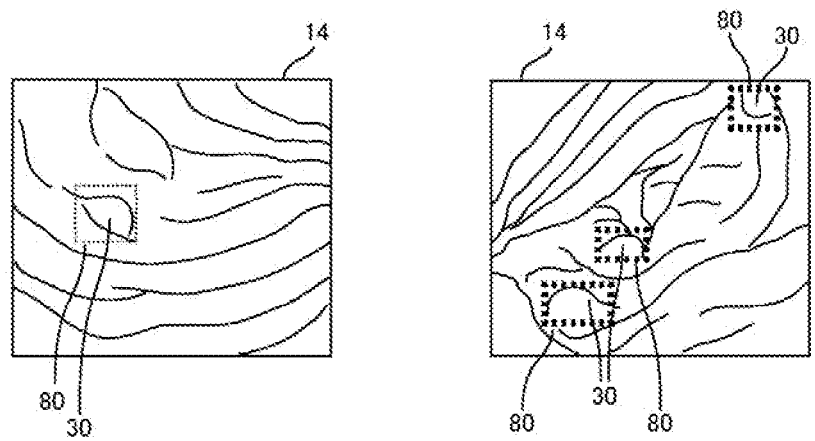
FIG. 9 is a diagram illustrating variation of highlighting.
Figure 10:
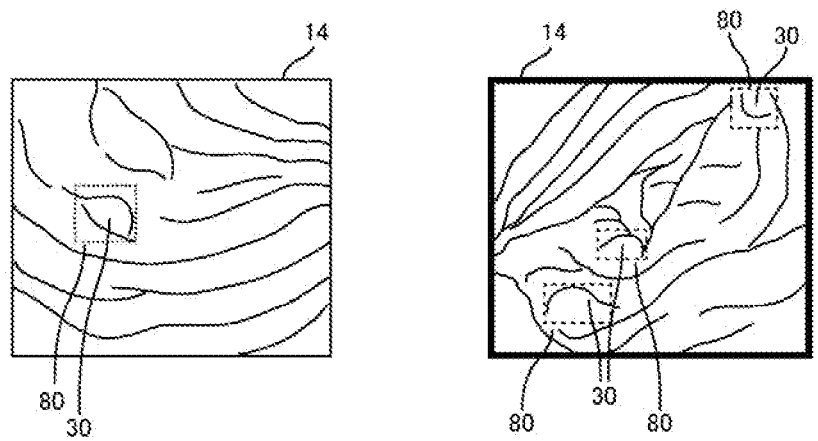
FIG. 10 is a diagram illustrating variation of highlighting.
Figure 11A:
FIG. 11A-11F are diagrams illustrating marks that are applied to abnormal regions.
Figure 11B:
Figure 11C:
Figure 11D:
Figure 11E:
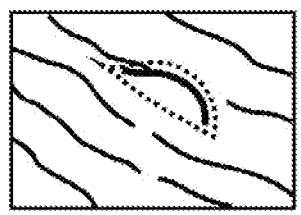
Figure 11F:

FIGS. 9 and 10 are diagrams illustrating variation of highlighting. There are various methods of highlighting. In FIG. 9, highlighting is performed for the frame surrounding the abnormal region 30. Specifically, the output unit 2040 performs highlighting by making the thickness of the frame 80 in a case where the number of detections is equal to or greater than the threshold value (in FIG. 9, the threshold value=2) thicker than the thickness of the frame 80 in a case where the number of detections is less than the threshold value. It should be noted that, instead of changing the thickness of the frame, a shape or a color of the frame may be changed or a color with which the frame is colored may be changed.

In FIG. 10, highlighting is performed for the frame of the moving image frame 14. Specifically, the output unit 2040 performs highlighting by thickening the frame of the moving image frame 14 in a case where the number of detections is equal to or greater than the threshold value more than the frame of the moving image frame 14 in a case where the number of detections is less than the threshold value. In this case, instead of changing the thickness of the frame, a color of the frame or a color with which the frame is colored may be changed. Alternatively, highlighting may be realized such that the frame is applied to the moving image frame 14 in a case where the number of detections is equal to or greater than the threshold value and the frame is not applied to the moving image frame 14 in a case where the number of detections is less than the threshold value.

It should be noted that, since the frame is applied to the moving image frame 14, the output information in the case of FIG. 10 is an image, in which the moving image frame 14 is included, as in the case of FIG. 7 or 8.

Here, a plurality of threshold values of the number of detections may be provided. In this case, the output unit 2040 performs highlighting according to a maximum threshold value satisfying "the number of detections≥the threshold value". Here, it is preferable that, as the maximum threshold value satisfying "the number of detections≥the threshold value" is greater, more highlighted display (that is, display that is likely to attract person's attention) is used. For example, as the maximum threshold value satisfying "the number of detections≥the threshold value" is greater, the thickness of the frame 80 is made thicker or a color that is likely to attract person's attention is used for the frame 80.

For example, it is assumed that two threshold values T1 and T2 are provided, and T1>T2. In this case, three cases of 1) the number of detections≥T1, 2) T1>the number of detections≥T2, and 3) the number of detections<T2 are considered. In this case, the output unit 2040 performs highlighting in the cases 1) and 2). As the display of the case 1), display that is more likely to attract person's attention than the display of the case 2) is used.

For example, in general, there are red and yellow as a color that is used for alert. Then, a case of using red often draws person's attention more strongly than a case of using yellow. Now, for example, the output unit 2040 sets the color of the frame 80 to red in the case 1) and sets the color of the frame 80 to yellow in the case 2). In the case 3) where the number of detections is less than the threshold value, the color of the frame 80 may be set to a color representing a comparatively safe situation, such as green. For example, the threshold value T2 is set to 2, and the threshold value T1 is set to 3. In this case, the frame 80 is green in a case where the number of detections is 1, the frame 80 is yellow in a case where the number of detections is 2, and the frame 80 is red in a case where the number of detections is equal to or greater than 3.

In addition, for example, the output unit 2040 may increase the thickness of the frame 80 in an order of the case 1), the case 2), and the case 3).

It should be noted that, in the above-described description, although the rectangular frame 80 is applied to abnormal region 30, the present invention is not limited to the rectangular frame being applied to the abnormal region 30, and any mark can be applied. FIG. 11 is a diagram illustrating marks that are applied to the abnormal regions 30.

For example, the output unit 2040 outputs the highlighted moving image frame 14 to the display apparatus. In addition, for example, the output unit 2040 may store the highlighted moving image frame 14 in the storage apparatus.

<<Output of Sound>>

For example, the output unit 2040 outputs alarm sound according to the number of detections. For example, the output unit 2040 outputs alarm sound to a speaker or the like connected to the information processing apparatus 2000.

Here, alarm sound may be output only in a case where the number of detections is equal to or greater than the threshold value or alarm sound may be output even in a case where the number of detections is less than the threshold value. In the latter case, the output unit 2040 uses different kinds of alarm sound between a case where the number of detections is equal to or greater than the threshold value and a case where the number of detections is less than the threshold value.

It is preferable that alarm sound in a case where the number of detections is equal to or greater than the threshold value is more likely to attract person's attention than alarm sound in a case where the number of detections is less than the threshold value. For example, a length of alarm sound in a case where the number of detections is equal to or greater than the threshold value is set to be longer than a length of alarm sound in a case where the number of detections is less than the threshold value. In addition, for example, a volume of alarm sound in a case where the number of detections is equal to or greater than the threshold value is set to be greater than a volume of alarm sound in a case where the number of detections is less than the threshold value.

Here, as in the case of highlighting, a plurality of threshold values of the number of detections may be provided. In this case, the output unit 2040 outputs alarm sound according to the maximum threshold value satisfying "the number of detections≥the threshold value". For example, as the maximum threshold value satisfying "the number of detections≥the threshold value" is greater, the length of alarm sound may be set to be longer or the volume of alarm sound may be set to be greater.

In addition, for example, the output unit 2040 may output sound that allows the recognition of the number of detections. For example, the output unit 2040 outputs sound ("1", "2", or the like) representing the number of detections. In addition, for example, the output unit 2040 may output alarm sound the same number of times as the number of detections.

Although the example embodiment of the present invention has been described referring to the drawings, the example embodiment is merely an example of the present invention. The present invention can employ a combination of the example embodiment or various configurations other than the above.

A part or the whole of the above-described example embodiments can be described as, but is not limited to, the following supplementary notes.

1. An information processing apparatus including:
   a detection unit that detects an abnormal region inside a body from a captured image in which the inside of the body is imaged; and
   an output unit that generates output information based on the number of the abnormal regions and outputs the generated output information.
2. The information processing apparatus described in 1, in which the output unit generates the output information including information indicating the number of the abnormal regions.
3. The information processing apparatus described in 2, in which the output unit includes an image, in which the information indicating the number of the abnormal regions is superimposed on the captured image, in the output information.
4. The information processing apparatus described in 3, in which, in a case where a plurality of abnormal regions are detected from the captured image, for each of the plurality of abnormal regions, the output unit superimposes the information indicating the number of the abnormal regions at a position having a predetermined relationship with the abnormal region.
5. The information processing apparatus described in 2, in which the output unit includes a second image, in which the captured image is included, in the output information, and
   the second image includes the information indicating the number of the abnormal regions outside the captured image.
6. The information processing apparatus described in 2, in which the output unit includes a second image, in which a plurality of the captured images having the abnormal region detected are included, in the output information, and
   for each of the plurality of the captured images, the second image includes the information indicating the number of abnormal regions detected from the captured image.

7. The information processing apparatus described in 1, in which the output unit generates the output information in which the captured image having the number of the abnormal regions equal to or greater than a threshold value is highlighted more than other captured images.

8. The information processing apparatus described in 7, in which the highlighting of the captured image is highlighting of the abnormal region included in the captured image or highlighting of the entire captured image.

9. The information processing apparatus described in 7 or 8, in which the output unit performs highlighting in different aspects between the output information in a case where the number of the abnormal regions is equal to or greater than a first threshold value and the output information in a case where the number of the abnormal regions is less than the first threshold value and is equal to or greater than a second threshold value.

10. The information processing apparatus described in 1 or 2, in which the output unit outputs sound determined based on the number of the abnormal regions as the output information.

11. The information processing apparatus described in 10, in which the output unit outputs different kinds of sound between a case where the number of the abnormal regions is equal to or greater than a threshold value and a case where the number of the abnormal regions is less than a threshold value.

12. A control method that is executed by a computer, the control method including:
a detection step of detecting an abnormal region inside a body from a captured image in which the inside of the body is imaged; and
an output step of generating output information based on the number of the abnormal regions and outputting the generated output information.

13. The control method described in 12, in which, in the output step, the output information including information indicating the number of the abnormal regions is generated.

14. The control method described in 13, in which, in the output step, an image in which the information indicating the number of the abnormal regions is superimposed on the captured image is included in the output information.

15. The control method described in 14, in which, in a case where a plurality of abnormal regions are detected from the captured image, in the output step, for each of the plurality of abnormal regions, the information indicating the number of the abnormal regions is superimposed at a position having a predetermined relationship with the abnormal region.

16. The control method described in 13, in which, in the output step, a second image, in which the captured image is included, is included in the output information, and the second image includes the information indicating the number of the abnormal regions outside the captured image.

17. The control method described in 13, in which, in the output step, a second image, in which a plurality of the captured images having the abnormal region detected are included, is included in the output information, and for each of the plurality of the captured images, the second image includes the information indicating the number of abnormal regions detected from the captured image.

18. The control method described in 12, in which, in the output step, the output information in which the captured image having the number of the abnormal regions equal to or greater than a threshold value is highlighted more than other captured images is generated.

19. The control method described in 18, in which the highlighting of the captured image is highlighting of the abnormal region included in the captured image or highlighting of the entire captured image.

20. The control method described in 18 or 19, in which, in the output step, the output information in a case where the number of the abnormal regions is equal to or greater than a first threshold value and the output information in a case where the number of the abnormal regions is less than the first threshold value and is equal to or greater than a second threshold value are highlighted in different aspects from each other.

21. The control method described in 12 or 13, in which, in the output step, sound determined based on the number of the abnormal regions is output as the output information.

22. The control method described in 21, in which, in the output step, different kinds of sound are output between a case where the number of the abnormal regions is equal to or greater than a threshold value and a case where the number of the abnormal regions is less than a threshold value.

23. A program causing a computer to execute each step of the control method described in any one of 12 to 22.

This application is based upon and claims the benefit of priority from Japanese patent application No. 2018-169722, filed on Sep. 11, 2018, the disclosure of which is incorporated herein in its entirety by reference.

REFERENCE SIGNS LIST

10: camera
12: moving image data
14: moving image frame
20: display apparatus
22: display region
24: display region
30: abnormal region
40: scope
50: endoscope system
80: frame
90: display
1000: computer
1020: bus
1040: processor
1060: memory
1080: storage device
1100: input-output interface
1120: network interface
2000: information processing apparatus
2020: detection unit
2040: output unit

The invention claimed is:
1. An information processing apparatus comprising:
at least one memory configured to store instructions; and
at least one processor configured to execute the instructions to:

detect an abnormal region inside a body from a captured image in which the inside of the body is imaged;
generate output information based on a number of detected abnormal regions which are detected and output the generated output information;
generate the output information including information indicating the number of the detected abnormal regions; and
include a second image, in which the captured image is included, in the output information,
wherein the second image includes, outside the captured image, the information indicating the number of the detected abnormal regions.

2. The information processing apparatus according to claim 1,
wherein the processor is configured to output an image, in which the information indicating the number of the abnormal regions is superimposed on the captured image, in the output information.

3. The information processing apparatus according to claim 2,
wherein, in a case where a plurality of abnormal regions are detected from the captured image, for each of the plurality of abnormal regions, the processor is configured to superimpose the information indicating the number of the abnormal regions at a position having a predetermined relationship with the abnormal region.

4. The information processing apparatus according to claim 1,
wherein
for each of the plurality of the captured images, the second image includes, outside the captured image, the information indicating the number of the detected abnormal regions.

5. The information processing apparatus according to claim 1,
wherein the at least one processor is configured to execute the instructions to generate the output information in which the captured image having the number of the detected abnormal regions equal to or greater than a threshold value is highlighted more than other captured images.

6. The information processing apparatus according to claim 5,
wherein the highlighting of the captured image is highlighting of the abnormal region included in the captured image or highlighting of the entire captured image.

7. The information processing apparatus according to claim 5,
wherein the at least one processor is configured to execute the instructions to perform highlighting in different aspects between the output information in a case where the number of the detected abnormal regions is equal to or greater than a first threshold value and the output information in a case where the number of the detected abnormal regions is less than the first threshold value and is equal to or greater than a second threshold value.

8. The information processing apparatus according to claim 1,
wherein the at least one processor is configured to execute the instructions to output sound determined based on the number of the detected abnormal regions as the output information.

9. The information processing apparatus according to claim 8,
wherein at least one processor is configured to execute the instructions to output different kinds of sound between a case where the number of the detected abnormal regions is equal to or greater than a threshold value and a case where the number of the detected abnormal regions is less than the threshold value.

10. A control method that is executed by a computer, the control method comprising:
at least one memory storing instructions; and
at least one processor executing the instructions to:
detect an abnormal region inside a body from a captured image in which the inside of the body is imaged;
generate output information based on a number of detected abnormal regions which are detected and outputting the generated output information;
generate the output information including information indicating the number of the detected abnormal regions; and
include a second image, in which the captured image is included, in the output information, and
wherein the second image includes, outside the captured image, the information indicating the number of the detected abnormal regions.

11. The control method according to claim 10,
wherein, in the outputting, an image in which the information indicating the number of the abnormal regions is superimposed on the captured image is included in the output information.

12. The control method according to claim 11,
wherein, in a case where a plurality of abnormal regions are detected from the captured image, in the outputting, for each of the plurality of abnormal regions, the information indicating the number of the abnormal regions is superimposed at a position having a predetermined relationship with the abnormal region.

13. The control method according to claim 10,
wherein, in the outputting, a second image, in which a plurality of the captured images having the abnormal region detected are included, is included in the output information, and
for each of the plurality of the captured images, the second image includes the information indicating the number of abnormal regions detected from the captured image.

14. The control method according to claim 10,
wherein, in the outputting, the output information in which the captured image having the number of the abnormal regions equal to or greater than a threshold value is highlighted more than other captured images is generated.

15. The control method according to claim 14,
wherein the highlighting of the captured image is highlighting of the abnormal region included in the captured image or highlighting of the entire captured image.

16. A non-transitory computer-readable storage medium storing a program causing a computer to execute a control method comprising:
at least one memory configured to store instructions; and
at least one processor configured to execute instructions to:
detect an abnormal region inside a body from a captured image in which the inside of the body is imaged;
generate output information based on a number of detected abnormal regions which are detected and outputting the generated output information;
generating the output information including information indicating the number of the detected abnormal regions; and include a second image, in which the captured image is included, in the output information,
wherein the second image includes, outside the captured image, the information indicating the number of the detected abnormal regions.

\* \* \* \* \*